United States Patent
Pietrzkowski et al.

(12) United States Patent
(10) Patent No.: US 9,101,587 B2
(45) Date of Patent: Aug. 11, 2015

(54) SOLID BETALAIN COMPOSITIONS AND METHODS

(75) Inventors: Zbigniew Pietrzkowski, Aliso Viejo, CA (US); Wayne Carl Thresher, Ashhurst (NZ)

(73) Assignee: VDF Futureceuticals, Inc., Momence, IL (US)

( * ) Notice: Subject to any disclaimer, the term of this patent is extended or adjusted under 35 U.S.C. 154(b) by 1227 days.

(21) Appl. No.: 12/525,296

(22) PCT Filed: Jan. 31, 2008

(86) PCT No.: PCT/US2008/001418
§ 371 (c)(1),
(2), (4) Date: Nov. 17, 2009

(87) PCT Pub. No.: WO2008/094705
PCT Pub. Date: Aug. 7, 2008

(65) Prior Publication Data
US 2010/0076050 A1    Mar. 25, 2010

Related U.S. Application Data

(60) Provisional application No. 60/898,766, filed on Jan. 31, 2007.

(51) Int. Cl.
| | | |
|---|---|---|
| A61K 36/185 | (2006.01) | |
| A23L 1/00 | (2006.01) | |
| A23L 1/30 | (2006.01) | |
| A23L 2/08 | (2006.01) | |
| A61K 9/16 | (2006.01) | |
| A61K 9/19 | (2006.01) | |
| A61K 31/12 | (2006.01) | |

(52) U.S. Cl.
CPC ............. *A61K 36/185* (2013.01); *A23L 1/0035* (2013.01); *A23L 1/3002* (2013.01); *A23L 2/08* (2013.01); *A61K 9/1652* (2013.01); *A61K 9/19* (2013.01); *A61K 31/12* (2013.01); *A23V 2002/00* (2013.01)

(58) Field of Classification Search
CPC .............................. A61K 2300/00; A61K 8/97
USPC ........................................................ 424/725
See application file for complete search history.

(56) References Cited

U.S. PATENT DOCUMENTS

| | | | |
|---|---|---|---|
| 4,027,042 A | 5/1977 | von Elbe et al. | |
| 4,238,518 A | 12/1980 | Poisson | |
| 4,409,254 A | 10/1983 | Garin et al. | |
| 2003/0036565 A1* | 2/2003 | Parkin et al. | 514/683 |

FOREIGN PATENT DOCUMENTS

| | | |
|---|---|---|
| GB | 1559275 | 1/1980 |
| WO | 98/26792 | 6/1998 |

OTHER PUBLICATIONS

Yan-Xiang, G. et al., "Research progress on beltain", China Food Additives, Feb. 28, 2006, vol. 1, pp. 65-69.
Lee, Y.N., et al. "Purification and Concentration of Betalaines by Ultra Filtration and Reverse Osmosis", Journal of Food Science, Wiley-Blackwell Publishing, Inc., vol. 47, No. 2, Jan. 1, 1982, pp. 465-471, XP008094339.
Database WPI, Week 200612, Thomson Scientific, London. GB; AN 2006-114292 XP002676347 & JP 2006 028029 A (Nippon Tensai Seito KK) Feb. 2, 2006 (abstract), 2 pages.
Watson, J. R., "Seasonal changes in betalaine concentrations and genetic analyses of variation in betalaine and sugar concentrations in roots of table beets (*Beta vulgaris* L.)" Dissertation Abstracts International, University of Wisconsin, Madison, vol. 42. No. 5, Nov. 5, 1981, XP009159596, 1 page.
VDF Futureceuticals, Inc., European Patent Publication EP08725107 published Nov. 11, 2009, Supplementary European Search Report dated Jun. 11, 2012, 1 pg.

\* cited by examiner

*Primary Examiner* — Chris R Tate
*Assistant Examiner* — Randall Winston
(74) *Attorney, Agent, or Firm* — Fish & Tsang LLP

(57) ABSTRACT

Solid, free-flowing, and substantially completely dissolvable preparations with high betalain content are presented. Most typically, the betalain profile of the preparations is near natural and includes betalains in an amount of between 10-40 wt %. As the preparations of the inventive subject matter maintain chemical stability and flowability over extended periods of time, it should be noted that the betalain preparations are now amenable to compounding in small and measured quantities. Furthermore, new biological activities of betalains are shown, and especially include significant induction of SIRT and reduction of serum triglyceride.

13 Claims, 2 Drawing Sheets

SOLID BETALAIN COMPOSITIONS AND METHODS

This application claims the benefit of U.S. provisional patent application with the Ser. No. 60/898,766, which was filed Jan. 31, 2007 and is incorporated herewith in its entirety.

FIELD OF THE INVENTION

The field of the invention is nutritional compositions and methods therefor, especially as they relate to highly concentrated free-flowing dry betalain compositions with substantially complete solubility.

BACKGROUND OF THE INVENTION

Red beets have long been a common source of various nutrients, and particularly of sugar and betaine. Further useful compounds obtained from red beet include betalains which represent a chemically diverse group of red to violet colored betacyanins (e.g., amaranthin, isoamaranthin, etc.) and typically yellow-colored betaxanthins (e.g., vulgaxanthin), which have found use as pharmaceutical and food coloring agents and as antioxidants.

Numerous manners of producing betalain preparations are known, and commonly start from comminuted beet root or root peelings. Other known source materials include root cell suspension culture, cactus pear, and selected higher fungi. Where betalains are prepared from beet juice or root macerates, preparations will typically have a betalain content of equal or less than 1 wt % and generally include significant quantities of sugars and other components. For example, WO 98/26792 describes various methods of preparing betalain extracts from root pulp that is further processed using crosslinked dextran chromatography. Alternatively, lyophilized beet can be used as starting material as described in US 2003/0036565, which is subsequently ground, solvent extracted, and subjected to crosslinked dextran chromatography to yield distinct betalain fractions. Typical known process employing spray drying of a beet juice concentrate will yield a powder comprising about 0.4 wt % betalains. Consequently, while most of these processes are conceptually simple, the concentration of betalains is generally below 1 wt %. Moreover, substantial quantities of non-betalain material are present and require further purification or other processing for removal.

In still other known methods (e.g., U.S. Pat. No. 4,238,518 or GB patent 1 559 275), stabilized betanidine extracts are prepared using ion exchange chromatography in which, among other compounds, betaxanthins are removed to yield a concentrated pigment preparation that is then dehydrated, re-dissolved, and combined with a stabilizing agent to form a thermally stable pigment powder. Such method advantageously allows for production of a relatively concentrated dry form of beet pigments, however, removes significant portions of the betaxanthins and certain betacyanins. Similarly, Garin et al. describe in U.S. Pat. No. 4,409,254 a process in which beet root extract is subjected at very low pH to chromatography using a non-ionic resin to so produce a concentrated eluate that is concentrated in betanin and other adsorbed solids. Such concentrated liquids may comprise 4.5 wt % betanin and can be dried to a betanin content of about 25 wt %. Unfortunately, such preparations are generally hygroscopic, readily clump, and tend to deteriorate relatively quickly.

In an effort to reduce sugar content of a betalain preparation, von Elbe et al. describe in U.S. Pat. No. 4,027,042 a process in which beet juice or beet pulp is subjected to a yeast fermentation to reduce sucrose concentration. While such process yields a concentrated pigment preparation and successfully eliminates sucrose, other fermentation byproducts are introduced, which are chemically unidentified and account for 25 wt % (or even more) of the final product.

Unfortunately, compounding and storage of currently known betalain preparations are negatively affected by the non-betalain components. For example, betalains prepared from freeze-dried beet juice are often clumpy and highly hygroscopic. Therefore, such preparations are notoriously difficult to weigh out and aliquot, especially where relatively small quantities are distributed. Worse yet, most of the currently known dry betalain preparations are limited to betalain concentrations of about 1 wt % (total betalains), and almost all of the attempts to increase the betalain concentration by extraction or other means also leads to an increase of hygroscopicity and clumping. In still other known preparations, and particularly in those with relatively high betalain content, non-betalain components will typically lead to substantial loss of stability in the absence of a stabilizing agent. Moreover, and often irrespective of the betalain content, non-betalain components are typically associated with resistance of the betalains to completely dissolve in aqueous media.

Therefore, while numerous compositions and methods of solid betalain preparations are known in the art, all or almost all of them suffer from disadvantages. Consequently, there is still a need to provide improved compositions and methods for solid betalain preparations.

SUMMARY OF THE INVENTION

The present invention is directed to solid, free-flowing, and readily dissolving betalain preparations in which the betalain concentration is relatively high. Most preferably, the total betalain concentration is at least 2 wt %, more preferably, at least 5 wt %, even more preferably at least 10 wt %, and most preferably at least 20 wt % at a betalain to sugar ratio of at least 0.3, more preferably at least 1.0, and most preferably at least 2.0. Betalain preparations according to the inventive subject matter will readily and substantially completely dissolve in water at high concentrations (typically at least 90%-98% at 50-100 mg/ml).

In preferred aspects of the inventive subject matter, the chemically distinct betalains in the betalain preparation has a near natural composition and/or has a concentration of between at least 10-20 wt %. In further preferred aspects, the betalain to sugar ratio is between 0.5 and 4.0, and most preferably at least 1.0. While not limiting to the inventive subject matter, the preparations contemplated herein will have a residual water content of less than 15 wt %.

Particularly contemplated solid compositions are free-flowing, which is characterized by the composition to allow comminuting to a size suitable to allow at least 90% of the composition to pass through a 30 mesh sieve, and more typically even through a 60 mesh sieve. Surprisingly, the flowability of contemplated compositions is maintained over extended periods, even when the compositions are stored at ambient conditions. Therefore, in certain aspects the free flowing is characterized by the ability of the composition, after comminuting of the composition to a size suitable to allow at least 90% of the composition to pass through a 60 mesh sieve, to allow at least 50%, and more typically at least 80% of the composition to flow through the 60 mesh sieve after storage for at least 2 weeks at 75° F. and 50% relative humidity. Consequently, nutritional supplements can now be formulated or compounded that provide between 20 and 500 mg of total betalains in a daily dose of less than 1000 mg.

Viewed from a different perspective, solid particulate compositions are contemplated that include a near-natural extract of betalains in an amount of at least 5.0 wt % coupled to a nutritionally acceptable carrier, wherein the carrier is present in an amount of equal or less than 98.0 wt % of the composition, and wherein at least 95 wt % of the composition is soluble within less than 2 minutes in water at a concentration of at least 50 mg/ml. In such compositions, the concentration of betalains is preferably at least 10.0 to 20.0 wt %, the nutritionally acceptable carrier is a polysaccharide, and the composition is free-flowing. Alternatively, the carrier is present in an amount of between 10 wt % to 40 wt %, and the near-natural extract of betalains is present in an amount of at least 8.0 wt %. It is further generally preferred that the particles in contemplated compositions have a size suitable to allow at least 90% of the composition to pass through a 60 mesh sieve, and that the composition is formulated such that at least 50% of the composition flow through a 60 mesh after storage for at least 2 weeks at 75° F. and 50% relative humidity. Therefore, contemplated compositions may be formulated as a nutritional supplement that is formulated to provide between 20 and 500 mg of total betalains in a daily dose of less than 1000 mg.

In further contemplated aspects, a method of producing a nutritional supplement includes a step of compounding contemplated compositions with a nutritionally acceptable carrier to form a supplement, and a step of providing information that the betalains are effective in a human subject to reduce serum triglyceride concentration, inhibit NF-kB, and/or stimulate SIRT in the human subject when administered to the subject. In further preferred aspects, the betalains are present in the supplement at a concentration effective to reduce oxidation of LDL cholesterol, increase HDL cholesterol, and/or decrease LDL cholesterol, most typically in an amount of between 5 mg and 200 mg per recommended daily intake of the supplement.

Various objects, features, aspects and advantages of the present invention will become more apparent from the following detailed description of preferred embodiments of the invention.

DETAILED DESCRIPTION

Figure 1:
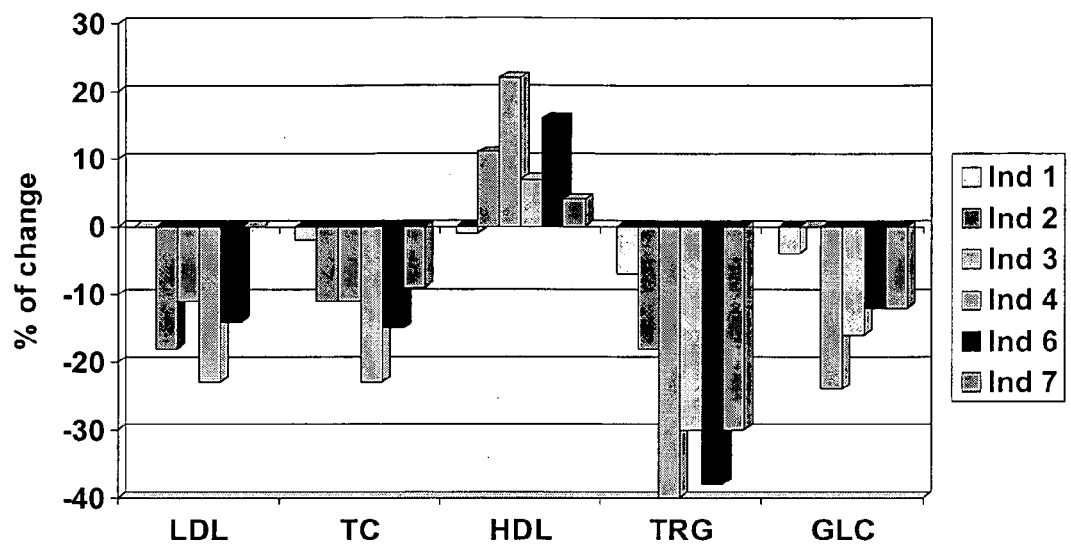
FIG. 1 is a graph depicting selected serum parameters of human volunteers treated with one exemplary composition of the inventive subject matter.

The inventors have discovered that various dry (i.e., non-liquid) betalain compositions can be prepared from beet juice or other liquid betalain-containing media by concentrating the betalains first on certain hydrophobically modified resins. Unexpectedly, the modified resins appear to remove a significant fraction of non-betalain components that would otherwise lead to clumping, instability, and/or resistance to complete dissolution in aqueous solvents. The so obtained compositions exhibit remarkably high concentrations of betalains (e.g., greater than 20 wt %) at significantly increased chemical stability while at the same time allowing to form a free-flowing powder that maintains flowability over extended periods of time, even when stored at ambient conditions. Moreover, the betalain compositions according to the inventive subject matter will readily and substantially completely dissolve in an aqueous solvent, even at high concentrations.

It should be especially appreciated that, to the best of the inventors' knowledge, the above advantages have not been achieved with heretofore known betalain compositions as such compositions typically had relatively low betalain content (typically below 1 wt %) and significant chemical instability, or where the concentration was relatively high, could not be powderized and/or maintained as dry powder with free-flowing character. Almost invariably, known betalain compositions with relatively high betalain content will readily clump and fail to rapidly dissolve, which up to this point prevented measured distribution of dry betalain compositions in small and controlled quantities.

In one aspect of the inventive aspect of the inventive subject matter, the inventors have discovered that a free-flowing solid betalain composition can be prepared that includes a plurality of chemically distinct betalains at a total betalain concentration of at least 2.0 wt % and a betalain to sugar ratio of at least 0.3. Such compositions are solid compositions that are at least 90 wt % (more typically at least 95%, and most typically at least 98%) soluble when dissolved in water at a concentration of at least 50-100 mg/ml. The term "free-flowing" as used herein means that at least 90% of a plurality of separate and individual particles will remain separate and individual in a bulk container when stored over a period of 24 hours at ambient temperature and humidity (75° F. and 50% relative humidity). Thus, a free-flowing small particle powder can be poured from a container in a continuous flow in which substantially the same mass leaves the container in the same time interval. In contrast, non-free-flowing materials will clump together to form aggregates of undefined size and weight and therefore can not be poured from the container in a continuous flow in which substantially the same mass leaves the container in the same time interval.

In more typical examples according to the inventive subject matter, the dry betalain composition has a total betalain concentration of at least 4.0 wt %, more typically at least 10.0 wt %, even more typically at least 15.0 wt %, and most typically at least 20.0 wt %. It should be noted that the chemical composition of the betalain preparations according to the inventive subject matter is a complex composition that includes a plurality of chemically distinct betalains. Thus, the complex preparation will include both betaxanthins and betacyanins. Most preferably, the betalain preparations presented herein have a near natural composition (i.e., no single betacyanin or betaxanthin originally present in the red beet is concentrated or depleted more than 30% [and more typically more than 15-20%] relative to the natural composition). Analysis of betalains and complex compositions can be performed as described by Corke et al (J Chromatogr Sci. 2005 October; 43(9):454-60) or Pourrat et al. (Journal of Food Science 53 (1), 294-295). Thus, typical preparations will include at least ten, more typically at least twenty, and most typically at least 25 chemically distinct betalains.

Depending on the particular source material and solvents used, it should be noted that the betalain to sugar ratio in contemplated compositions is least 0.3, more typically at least 0.5, even more typically at least 1.0, and most typically at least 2.0. Viewed from a different perspective, most preferred preparations will have a betalain to sugar ratio between 1.0 and 5.0, and even more typically between 2.5 and 4.5.

With respect to the remaining sugars in contemplated compositions it should be recognized that the chemical nature will vary and depend on the starting material and work-up. However, most typical remaining sugars include may be mono-, oligo, and/or polysaccharides, sugar alcohols, and pectins. Thus, it should be appreciated that where the oligo, and/or polysaccharide concentration is to be reduced, enzymatic or fermentative processes may be used to achieve such reduction. Alternatively, or additionally, residual monosaccharides may be removed using various manners known in the art, including ultrafiltration, molecular sieving, and/or enzymatic conversion.

With respect to residual water content of contemplated compositions, it is generally preferred that the water content is low enough to allow the product to be free-flowing in powder or otherwise comminuted form. Therefore, numerous methods of drying are deemed suitable and include air drying, freeze-drying, drum drying, etc. Typically, the residual water content is equal or less than 20 wt %, more typically equal or less than 15 wt %, and most typically equal or less than 10 wt %. Furthermore, it should be noted that depending on the particular manner of drying, contemplated compositions may be comminuted or otherwise ground to form a powderized product that is easily compounded, mixed, or otherwise dispensed. Such comminuted form will preferably have similar size of particles, and it is especially preferred that at least 60%, and more typically at least 80% of the particles have a size variation of less than 20% as measured in the longest dimension. For example, preferred compositions may be processed such that at least 50% (and more preferably 60%, 70%, 80%, 90%, and even more) of the composition flow through a 18 mesh, more preferably 30 mesh, and most preferably 60 mesh sieve (US mesh, with the numeral denoting sieve number). Therefore, especially contemplated processing includes cutting, grinding, and milling. On the other hand, and especially where the drying process includes spray drying, it is contemplated that the so produced product will have an average particle size of between 20-800 micron, more typically between 50-500 micron, and most typically between 100-300 micron.

It should be particularly appreciated that the compositions and methods according to the inventive subject matter unexpectedly allow for production of a betalain composition that has and maintains free-flowing character for extended periods of time, even when such complex compositions are stored at ambient conditions. While not wishing to be bound by any theory or hypothesis, the inventors contemplate that use of the specific hydrophobically modified chromatographic supports in the preparation of the betalain extracts allowed for removal of most, or even all of the compounds that would otherwise lead to clumping, high residual water content, hygroscopicity, lack of chemical stability, and other undesired effects associated with known complex betalain compositions, and especially concentrated (e.g., at least 2 wt %, more typically at least 10 wt %) betalain compositions.

Among numerous hydrophobic modifications that did not produce desirable product parameters, certain hydrophobic modifications unexpectedly produced desirable product parameters. These modifications included those in which the modifying group had multiple rings with generally planar configuration and in which at least one ring had aromatic character (most preferably a benzoquinone group or benzoquinoid structure in which one oxygen atom is replaced by a group into which pi electrons of the ring can delocalize). Remarkably, seemingly closely related other hydrophobic structures immobilized on a resin (e.g., organic polymer or silica) failed to provide products with desirable parameters.

Again, while not limiting to the inventive subject matter, the inventors contemplate that betalains will associate with the modifications resin via "pi-stacking" while allowing undesirable compounds to pass. In further aspects of the inventive subject matter, the hydrophic modification was covalently coupled to the resin (silica or styrene, appropriately activated where required [e.g., using gamma-aminopropylsilane for silica or chloromethylated or anhydride activated styrene]), preferably via a linking moiety having a length equivalent to at least 3 carbon-carbon bonds.

For example, and using such hydrophobically modified chromatographic supports, the compositions prepared as further described below could be stored for extended periods at controlled ambient conditions (75° F. and 50% relative humidity) for at least 2 days, more typically for between 2 days and two weeks, and most typically for between 2 weeks and 2 months (and even longer) without loss of the free-flowing character and apparent degradation. Such compositions had a betalain content of typically between 2-5 wt %, more typically between 5-10 wt %, and most typically between 10-40 wt %. Remarkably, even after prolonged storage, at least 60-70%, more typically at least 80%, and most typically at least 90% will flow through the same mesh filter. Moreover, solubility (at least 90% of the betalain composition, more typically at least 92%, even more typically at least 95%) of so prepared betalain compositions exhibited remarkable water solubility, typically at least between 0.1 mg/ml and 1 mg/ml, more typically at least between 1 mg/ml and 10 mg/ml, even more typically at least between 10 mg/ml and 50 mg/ml, and most typically at least between 50 mg/ml and 100 mg/ml, and even higher.

In another example, the inventors have also discovered that a betalain composition can be prepared that is a particulate composition that comprises a near natural extract of betalains at a concentration of at least 2.0 wt % (and more typically at least 5 wt %) where the betalains are physically associated with a carrier at a concentration of equal or less than 98.0 wt % (and more typically less than 95 wt %), wherein the composition is a solid composition that is at least 90 wt % (and more typically at least 95 wt %) soluble when dissolved in water. Typically, such preparations are free-flowing and maintain free-flowing character for at least 2 weeks when stored at ambient conditions. With respect to preferred betalain concentrations and the chemically complex nature of the betalain preparations, the same considerations as above apply.

In particularly preferred aspects, the carrier is a nutritionally and/or pharmaceutically acceptable carrier at a relatively high weight percentage. Most typically (but not necessarily), the carrier is a soluble carrier and present at a concentration of between 10 wt % to 40 wt %, and the near natural extract of betalains is present at a concentration of at least 8.0 wt %. For example, the carrier may be (based on) a nutritionally acceptable water soluble saccharide, and most typically a polysaccharide. Alternative carriers may be insoluble and organic (e.g., modified starch) or inorganic (e.g., silica). In such preparations, it is generally preferred that the betalain preparation is derived from a mixture, slurry, or suspension that is then spray dried to the final free-flowing product.

Similar to the preparations above, it is typically preferred that the composition has a residual water content of less than 20 wt % (more typically less than 15 wt %, and even more typically less than 10 wt %), and that the preparation is formulated such that at least 50% of the composition flow through a 60 mesh after storage for at least 2 days at 75° F. and 50% relative humidity. More preferably, however, at least 60%, 70%, 80%, or even 90% and more will flow through such mesh (which may even be finer). Similarly, and especially where the betalain concentration is above 5 wt %, it is generally preferred that the above flow characteristics will maintained over more than 2 days of storage, including storage times of between 2 days and 2 weeks, and most preferably storage times between 2 weeks and 2 months (and even longer). Therefore, particles of the particulate composition will typically have a size that is suitable to allow at least 90% of the composition to pass through a 60 mesh sieve, and the composition is formulated such that at least 50% (and more typically at least 60%, 70%, 80%, or even 90% and more) of the composition flow through a 60 mesh after storage for at least 2 weeks at 75° F. and 50% relative humidity (US Standard mesh sizes are provided, e.g., in ASTM E-11-1987).

Regardless of the particular formulation, the inventors further discovered that the compositions according to the inventive subject matter have various remarkable, desirable, and heretofore unknown physiological activities when administered to a human. Among other effects, the inventors discovered that the compositions according to the inventive subject matter reduce serum triglyceride levels, increase the ratio of HDL/LDL cholesterol, reduce oxLDL concentration, and/or reduce and normalize blood glucose (fasting and under glucose challenge). Moreover, the compositions according to the inventive subject matter also significantly and in a concentration dependent manner inhibited NF-kB activity (in vitro). In yet further observed effects, contemplated betalain compositions also significantly increased SIRT (NAD-dependent deacetylase: mammalian homologue of Sir2 [silent information regulator 2]) expression. Most remarkably, SIRT stimulation was achieved at concentrations that were several orders of magnitude lower than comparable SIRT stimulation using resveratrol.

Therefore, contemplated compositions may be used in prophylaxis and/or treatment of various conditions, and especially those associated with elevated serum triglyceride levels, low the HDL/LDL cholesterol level, oxidation of LDL cholesterol, increased blood glucose, reduced glucose tolerance, and/or mitochondrial dysfunction. Further suitable conditions and diseases that will positively respond to administration of contemplated compositions include dyslipidemia, hypercholesterolemia, coronary artery disease, metabolic syndrome, obesity, and degenerative effects due to aging. While not limiting to the inventive subject matter, the inventors discovered that the betalain compositions when administered to human volunteers at relatively low dosages (e.g., 3 times 100 mg per day composition with a betalain content of about 30 wt %) significantly inhibited CETP activity in the bloodstream. Consequently, contemplated compounds may be administered to manage size of HDL particles and to increase the serum HDL concentration.

In further contemplated aspects, additional nutritional and/or pharmaceutical agents may be combined with the betalain preparations, and particularly include those that positively affect at least one of blood glucose and blood lipids. There are numerous such agents known in the art, and all of them are deemed suitable for use herein. However, especially preferred additional agents include insulinotropic agents, vitamins, minerals, and other plant extracts and preparations (e.g., sprout extract, coffee cherry extract, etc). For example, 4-hydroxy-isoleucine or chromium-containing compositions may be combined with contemplated betalain compositions, wherein the 4-hydroxyisoleucine may be synthetic, or more preferably, isolated or enriched from a seed extract (e.g., fenugreek seed), and wherein the chromium is preferably in a water-soluble complex matrix.

Thus, a method of assisting a human subject to reduce his or her serum triglyceride concentration may include a step of providing a composition comprising a betalain (or betalain mixture) at a concentration effective to reduce the serum triglyceride concentration. Such composition most preferably further reduce oxidation of LDL cholesterol in the human subject, increase HDL cholesterol, and/or decrease LDL cholesterol. In especially preferred methods, the betalains are present in an amount of between 5 mg and 200 mg per recommended daily dose.

Consequently, kits, nutritional supplements, and food items are contemplated that comprise an edible component that preferably includes the compositions contemplated herein and an instruction associated with the edible component that informs a person that oral consumption of the alimentary article stimulates SIRT, inhibits NF-kB, reduces total serum triglyceride concentration, and/or reduces oxidation of LDL cholesterol in a human subject. Where desirable, a self-test kit or instructions therefore may also be associated with the product to allow a user to test for various physiological parameters (e.g., oxLDL, HDL, LDL, total cholesterol, oxidative stress, triglyceride, blood glucose, etc.). While contemplated articles may be formulated in numerous manners, it is generally preferred that the article is formulated as a tablet, a capsule, a ready-to-mix formulation or a dragee. Alternative formulations also include oil infusions, soft gels, coatings for capsules, and liquid tinctures. Most preferably, contemplated betalain compositions are formulated as a nutritional supplement to provide between 20 and 500 mg of total betalains in a recommended daily dose, and where the supplement is a capsule, tablet, dragee, or other compact forming which the 20 to 500 mg of total betalains are administrable in a total amount of less than 1000 mg.

Furthermore, contemplated compositions may include the betalain compositions disclosed herein, in combination with at least one additional nutritionally beneficial ingredient. For example, and where appropriate, an insulinotropic agent (e.g., 4-OH-leu) is present in an amount of between 20 mg and 500 mg per recommended daily dose. Other ingredients include chemically defined compounds (e.g., vitamins, cofactors, minerals, soluble and insoluble fibers, agents that increase anabolism or catabolism), but also chemically complex mixtures and especially plant extracts. Among other contemplated extracts, coffee cherry preparations are especially preferred herein.

EXAMPLES

Exemplary Processes for Extraction

Option 1: Extraction started with commercially available beet juice (about 65 brix; obtained from SVZ International) having a total betalain content of about 0.6 wt % on dry basis. The juice was filtered to remove particulates and the filtrate was used without further modification for chromatography. A column was packed with a hydrophobically modified silica resin (commercially available as Resin HSI-564 from VDF Futureceuticals; Momence, Ill. 60954), and the filtered juice was passed through the column at between 1-50 bed volumes per hour at a loading with between 1-20 bed volumes. The pass fractions were discarded, and the betalains were eluted from the resin using a mild buffer at slightly basic pH (e.g., 0.1-0.2 M ammonium acetate in water, pH 8.2 to 8.4, at a temperature of 110° F., or 0.1-0.2 M ammonium carbonate in water at pH range 7.0 to 9.0, same temperature). The so obtained eluate was freeze-dried without further modification to a dry product. Quantitative analysis of the product revealed a total betalain content of about 15 wt % at 6 wt % total sugar and a residual water content of about 8 wt %. The dry product was then ground using a rotating blade grinder to form a powder product that was passed through a 60 mesh sieve. Most remarkably, more than 90%, and more typically more than 95% of the free-flowing dry product dissolved within less than 2 minutes at a concentration of between 0.1 mg/ml and 10 mg/ml, more typically at a concentration of between 10 mg/ml and 50 mg/ml, and more typically at a concentration of between 50 mg/ml and 100 mg/ml (and in some cases even higher, such as between 100 mg/ml and 200 ml/ml).

longer) storage at the defined condition, substantially the same amount (>90%) of the dry powder passed through a mesh sieve of same mesh size Analysis of Betalain Preparations Various commercially available betalain-containing preparations (Comp. 1 to Comp. 4) were analyzed for betalain concentration, sugar concentration, and hygroscopicity, and results are listed in the table below. Hygroscopicity was not determined for the comparative examples as they were too clumpy or a liquid.

| Composition | Betalain wt % UV | Sugar wt % | Ratio B/S | Hydroscopicity |
|---|---|---|---|---|
| Comp. 1: Air Dried Beet Powder | 0.565 (0.59, 0.54) | 54.2 (64.62, 43.72) | 0.01 (0.008-0.013) | N/C |
| Comp. 2: Beet Juice Concentrate 65 Brix | 0.587 (0.51, 0.48, 0.77) | 45.3 (44.36, 46.31) | | N/C |
| Comp. 3: Spray Dried Beet Powder | 0.43 | 32.6 (Not checked for maltose) | 0.013 | N/C |
| Comp. 4: Beet Juice Single Strength | 0.14 | 6 | 0.06 | N/C |
| Inventive Example | 22 (0.05-45.5) | 5-8 (0.0-82.5) | 3 (?) (2.75-4.4) | 6-12% moisture |

Even more remarkably, the product was stable over at least 2 weeks storage at 75° F. and 50% relative humidity without any observable changes in composition, free-flowability, or other parameters, and did not aggregate to larger particles or clumps. Indeed, after 2 weeks (and longer) storage at the defined condition, substantially the same amount (>90%) of the dry powder passed through a mesh sieve of same mesh size.

Option 2: Extraction started as above with commercially available beet juice (about 65 brix; obtained from SVZ International) having a total betalain content of about 0.6 wt % on dry basis. The juice was filtered to remove particulates and the filtrate was used without further modification for chromatography. A column was packed with a hydrophobically modified styrene resin (commercially available as Resin HST-226 from VDF Futureceuticals) and the filtered juice was passed through the column at between 1-50 bed volumes per hour at a loading with between 1-20 bed volumes. The pass fractions were discarded, and the betalains were eluted from the resin using a mild buffer at slightly basic pH (e.g., 0.1-0.2 M ammonium acetate in water, pH 8.2 to 8.4, at a temperature of 110° F., or 0.1-0.2 M ammonium carbonate in water at pH range 7.0 to 9.0, same temperature). Without drying as described above, the so obtained eluate was mixed with a water-soluble polysaccharide (e.g., to about 30 wt % maltodextrin final concentration) as carrier and spray-dried to a dry product having about 10 wt % betalains at 45 wt % total sugar content with a residual water content of about 5 wt %. The average particle size of the spray-dried product was about 150 micron (passed through 60 mesh sieve) and more than 90% (and more typically more than 95%) of the free-flowing dry product dissolved within less than 2 minutes at a concentration of between 0.1 mg/ml and 10 mg/ml, more typically at a concentration of between 10 mg/ml and 50 mg/ml, and more typically at a concentration of between 50 mg/ml and 100 mg/ml (and in some cases even higher, such as between 100 mg/ml and 200 ml/ml). As above, the product was stable over at least 2 weeks storage at 75° F. and 50% relative humidity without any observable changes in composition, free-flowability, or other parameters, and did not aggregate to larger particles or clumps. Once more, after 2 weeks (and Methods of Analysis: Betalain wt % was measured following UV spectroscopy as outlined in UV FCCM C.52.1. Sugar content in wt % was determined by HPLC as outlined in AOAC Method 982.14. Hygroscopicity was determined by placement of samples in relative humidity chambers of 32% (saturated Magnesium Chloride), 52% (Magnesium Nitrate) and 93% (Potassium Nitrate) at a temperature of 25° C. and subsequent check for wt % moisture after 72 hours of sample equilibration as outlined in FCCM P.1.1. The inventive example was prepared according to Option 1 above and was a free-flowing powder when prepared and stored at 52% relative humidity. The product had an average residual water content of 10.6%. Of course, it should be appreciated that further membrane filtration and other separation steps (or use of a more concentrated starting material) can be employed to further concentrate the compositions.

Trials with Human Volunteers

Two independent treatments on human volunteers were completed with four and three individuals, respectively. Each volunteer received a concentrated betalain composition in a 100 mg total dose containing about 30 mg total betalains, three times a day, for three consecutive days. No adverse effects were reported. Analysis of markers in serum included HDL, LDL, TC, Triglycerides, Glucose, and oxLDL. FIG. 1 depicts the results (GLC represents blood glucose: Individual 7 was 140/124 (before/after), Individual 4: 138/126 (before/after); TRG represents total triglycerides: Individual 7: 339/238 (before/after), Individual 4, 342/260 (before/after), Individual: >650/580 (before/after), Individual 3: 463/317 (before/after)). Therefore, 3 times a day administration of 100 mg of the composition according to the inventive subject matter shows significant effect, primarily on triglycerides but also on blood glucose.

Figure 2A:
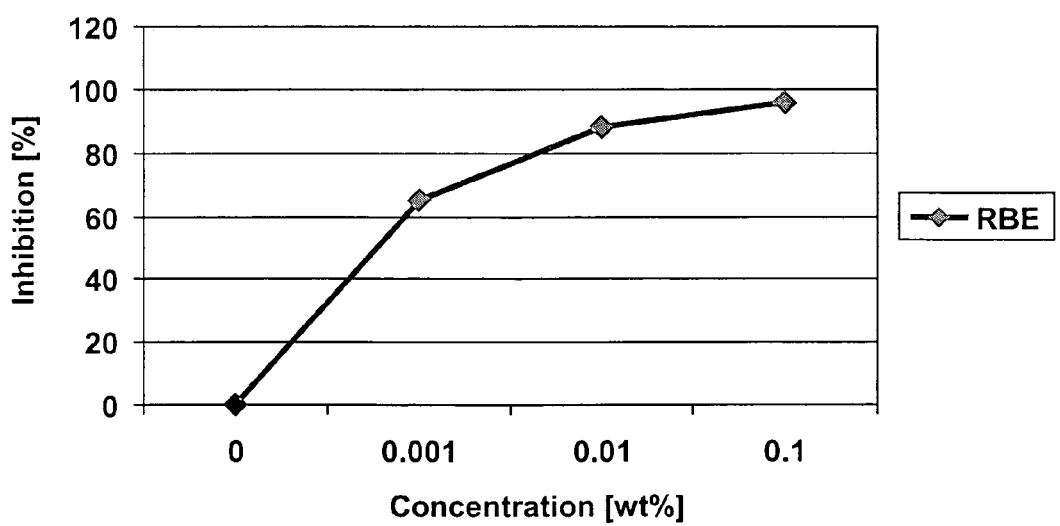
FIG. 2A is a graph depicting concentration-dependent inhibition of NF-kB in vitro using an exemplary composition of the inventive subject matter.

In Vitro Effects of Contemplated Compositions with about 30 Wt % Total Betalains FIG. 2A depicts exemplary results of concentration dependent in vitro inhibition of Nf-kB using compositions according to the inventive subject matter. Here, HL-60 cells were stimulated with 10 ng/mL of TNF-alpha to increase activity of Nf-kB and were used to establish baseline values. Addition of a betalain composition (indicated by wt % betalain in medium) prepared similar to Option 1 above resulted in strong and significant inhibition of TFN-alpha-induced Nf-kB activation in the dose dependent manner. Nf-kB activity level was measured by Elisa kit form Cayman Inc., and cell culture followed well known protocols.

Figure 2B:
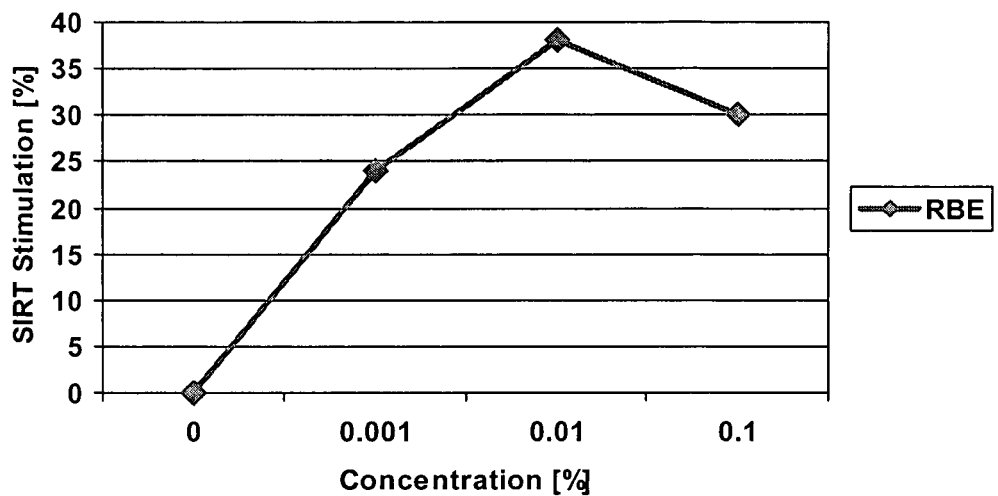
FIG. 2B is a graph depicting concentration-dependent stimulation of SIRT in vitro using an exemplary composition of the inventive subject matter.

FIG. 2B depicts exemplary results of concentration dependent in vitro stimulation of SIRT using compositions according to the inventive subject matter. More specifically, SIRT1 expression was monitored in HT-29 cells after treatment with the same composition as in the experiment above: HT-29 cells were treated in medium with the composition for 4 hrs prior to SIRT activity assay, which used a commercially available fluorescent substrate for SIRT (obtained from Biomol, Inc.). The experimental protocol followed essentially the protocol provided in the test kit. As is readily apparent, the compositions according to the inventive subject matter exhibited a strong and significant effect. Indeed, the below results demonstrate a strong stimulatory effect at a concentration that is only 2.2% of that for stimulation by resveratrol.

Figure 2C:
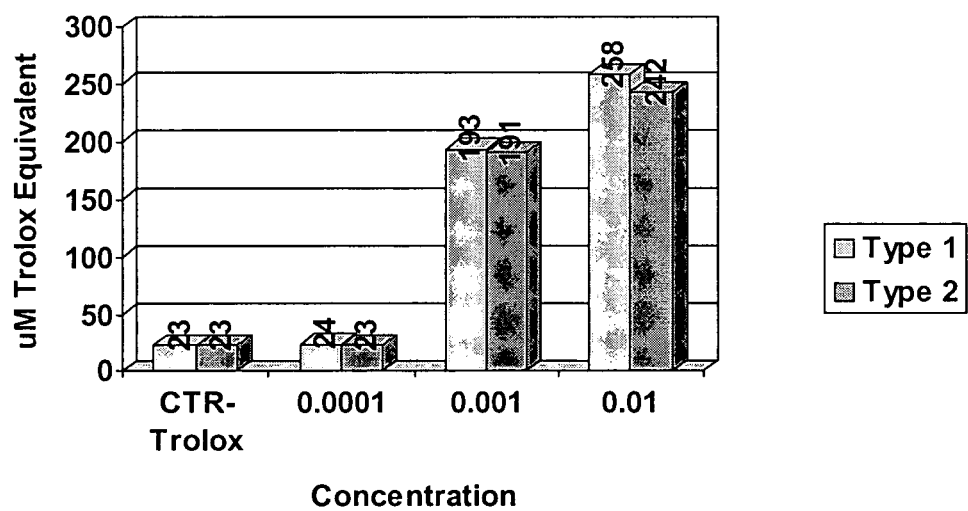
FIG. 2C is a graph depicting concentration-dependent change in ORAC values of human serum treated with two exemplary compositions of the inventive subject matter.

FIG. 2C depicts exemplary data showing strong and significant increase of ORAC (oxygen radical absorption capacity) values in human serum by contemplated compositions. Again, the increase in ORAC was concentration dependent and the RBE increase in ORAC was compared to Trolox (6-Hydroxy-2,5,7,8-tetramethylchroman-2-carboxylic acid) as control.

|  | Red Beet Extract | |
| --- | --- | --- |
| Parameter | Type 1 | Type 2 |
| Reductions of lipids | +++ | + |
| Glucose reduction | ++ | 0 |
| TRG Reduction | ++++ | + |
| SIRT Stimulation | (+++) | + |
| Nf-kB inhibition | + | +++ |
| Serum ORAC Increase | +++ | +++ |
| CRP Reduction | (+) | (+++) |
| oxLDL Reduction | (+) | (+++) |
| Total Distinct Betalains | 25 | 30 |

Thus, specific embodiments and applications of betalain compositions have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A solid composition for reducing serum triglyceride concentration, inhibiting NF-KB and stimulating SIRT said composition comprising effective amounts of a betalain ammonium salt and a sugar, wherein the betalain ammonium salt in the solid composition is at least 2.0 wt %, the betalain to sugar ratio is at least 0.3, and the composition is a free-flowing solid that is at least 90% soluble when dissolved in water at a concentration of at least 50 mg/ml.

2. The composition of claim 1 wherein the free-flowing solid composition is comminuted to a size suitable to allow at least 90% of the solid composition to pass through a 30 mesh sieve.

3. The composition of claim 1 wherein the free-flowing solid composition is comminuted to a size suitable to allow at least 90% of the solid composition to pass through a 60 mesh sieve.

4. The composition of claim 3 wherein the free-flowing solid composition, after comminuting to a size suitable to allow at least 90% of the solid composition to pass through a 60 mesh sieve, at least 50% of the solid composition is allowed to flow through the 60 mesh sieve after storage of the solid composition for at least 2 weeks at 75° F. and 50% relative humidity.

5. The composition of claim 3 wherein the free-flowing solid composition, after comminuting to a size suitable to allow at least 90% of the solid composition to pass through a 60 mesh sieve, at least 80% of the solid composition is allowed to flow through the 60 mesh sieve after storage of the solid composition for at least 2 weeks at 75° F. at 50% relative humidity.

6. The composition of claim 1 wherein the concentration of betalain ammonium salt is at least 10.0 wt %.

7. The composition of claim 1 wherein the betalain ammonium salt to sugar ratio is at least 1.0.

8. The composition of claim 1 wherein the solid composition is formulated as a nutritional supplement, and wherein the supplement provides between 20 mg and 500mg of betalain in a daily dose that is less than 1000 mg.

9. A method of producing a nutritional supplement comprising the steps of: mixing the solid composition of claim 1 with a nutritionally acceptable carrier to form the nutritional supplement, wherein the supplement is in an amount effective to reduce serum triglyceride concentration, inhibit NF-KB and stimulate SIRT in a human subject in need thereof when administered to the subject.

10. The method of claim 9 wherein at least 50% of the solid composition is allowed to flow through a 60 mesh sieve after storage of the solid composition for at least 2 weeks at 75° F. and 50% relative humidity.

11. The method of claim 9 wherein at least 80% of the solid composition is allowed to flow through a 60 mesh sieve after storage of the solid composition for at least 2 weeks at 75° F. and 50% relative humidity.

12. The method of claim 9 wherein the betalain ammonium salt is present in the nutritional supplement at a concentration effective to reduce oxidation of LDL cholesterol, increase HDL cholesterol, and decrease LDL cholesterol.

13. The method of claim 9 wherein the betalain ammonium salt is present in the nutritional supplement in an amount of between 5 mg and 200 mg per recommended daily intake of the supplement.

* * * * *